United States Patent [19]
Kitrilakis et al.

[11] Patent Number: 4,535,778
[45] Date of Patent: Aug. 20, 1985

[54] METHOD AND APPARATUS FOR DETECTING BLOOD GAS

[75] Inventors: Sotiris Kitrilakis, Berkeley; Theodore R. Johnson, Point Reyes, both of Calif.

[73] Assignee: Ancet Corporation, Richmond, Calif.

[21] Appl. No.: 494,534

[22] Filed: May 13, 1983

[51] Int. Cl.³ .............................................. A61B 5/00
[52] U.S. Cl. ................................. 128/635; 204/403; 204/415; 204/431
[58] Field of Search .............. 128/635, 637, 639, 632, 128/787; 204/403, 415, 431

[56] References Cited

U.S. PATENT DOCUMENTS

| | | | |
|---|---|---|---|
| Re. 31,440 | 3/1974 | Eberhard et al. | 128/635 |
| 2,168,867 | 8/1939 | George | 128/635 |
| 3,769,961 | 11/1973 | Fait et al. | 128/635 |
| 3,957,613 | 5/1976 | Macur | 128/635 |
| 4,094,305 | 6/1978 | Kessler | 128/635 |
| 4,273,636 | 6/1981 | Shimada et al. | 128/635 |
| 4,296,752 | 10/1981 | Welsh et al. | 128/635 |
| 4,304,453 | 12/1981 | Grunwald | 128/639 |
| 4,305,399 | 12/1981 | Beale | 128/635 |
| 4,319,578 | 3/1982 | Enger | 128/635 |
| 4,396,017 | 8/1983 | Deply et al. | 128/635 |

Primary Examiner—Lee S. Cohen
Assistant Examiner—Steven Falk
Attorney, Agent, or Firm—Lothrop & West

[57] ABSTRACT

A blood gas detector for human use has a support fitting into the mouth between the sides of the upper and lower jaws and the inside of the cheek and carries electric conductors for connection to an external indicator affording response to blood gas present at the inside of the cheek. The detector may also have an electric heater on the support fitting.

9 Claims, 6 Drawing Figures

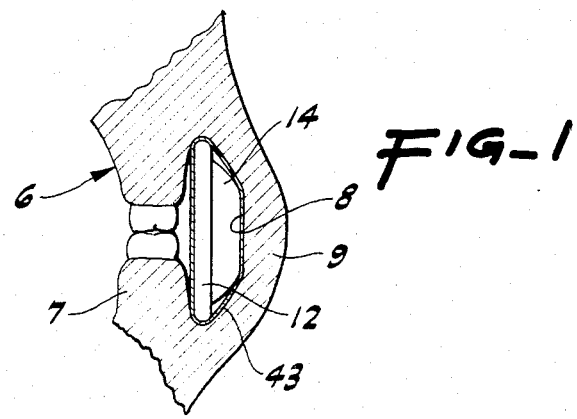
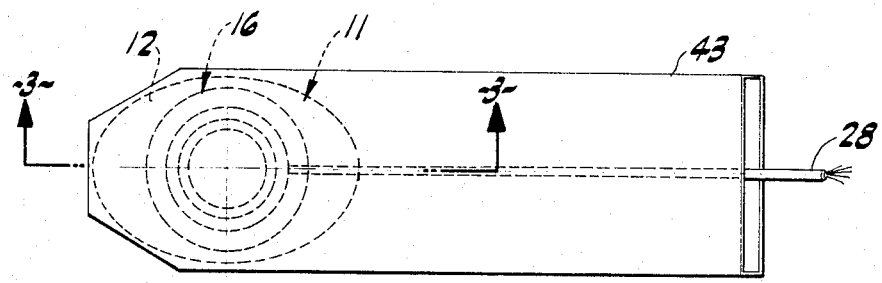
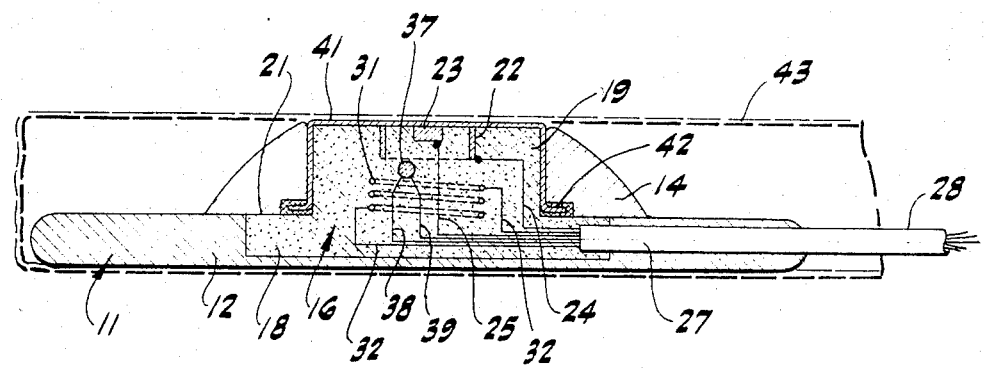

METHOD AND APPARATUS FOR DETECTING BLOOD GAS

BRIEF SUMMARY OF THE INVENTION

A blood gas detector especially for detecting gases, such as oxygen or carbon dioxide, in human blood has a base plate shaped and sized to be received and temporarily retained in the human mouth, preferably between the outside of the jaws and the adjacent inside of the cheek. An included heater increases the local skin temperature of the inside of the cheek and circulation of the contained blood. Electrodes responsive to oxygen locally present establish an electric current affecting and external blood gas indicator.

PRIOR ART OF INTEREST

The most pertinent prior art known at present to the applicants consists of the patent to Eberhard et al. U.S. Pat. No. 3,795,239 issued Mar. 5, 1974, and the publication "Continuous Transcutaneous Blood Gas Monitoring", The National Foundation—March of Dimes, Birth Defects: Original Article Series, Volume XV, Number 4, 1979, published by Alan R. Liss, Inc., New York.

The Eberhard et al. patent is concerned with blood oxygen detection and operates on the external or exposed surface of the human skin and, while an effective device, is relatively slow in operation and is subject to some other deleterious factors.

The device of the publication is a lip clamp and has a disadvantage, as noted in the article, that the vascular network is pinched in the very area where vascular freedom and expansion are beneficial.

BRIEF DESCRIPTION OF THE SEVERAL VIEWS OF THE DRAWINGS

FIG. 1 is a partial diagram in cross-section on a substantially vertical transverse plane through a part of the human jaw structure and associated cheek with a portion of the device of the invention in place.

FIG. 2 is a plan of one form of blood oxygen detector pursuant to the invention.

FIG. 3 is a cross-section, the plane of which is indicated by the lines 3—3 of FIG. 2.

DETAILED DESCRIPTION

Figure 4:
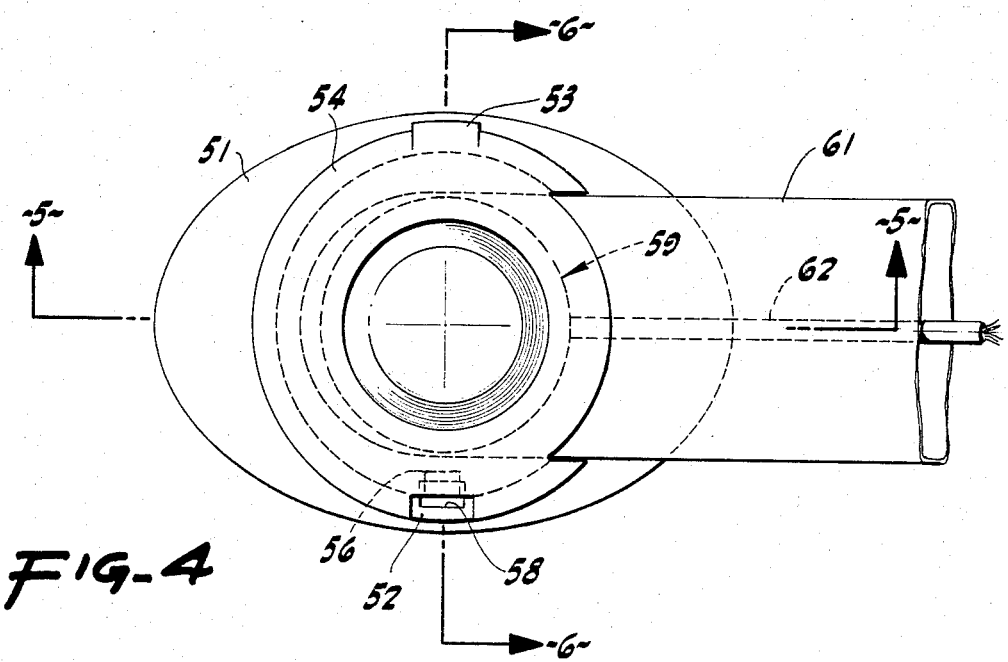
FIG. 4 is a view in plan of an alternate version of the blood gas detector of the invention.

Pursuant to the present invention, there is provided a sensing means especially adapted to be received easily and freely in the human mouth, particularly in and close to a chosen zone between the outer portion of the upper jaw 6 and the lower jaw 7 and the adjacent inner wall 8 of the cheek 9. This location is favorable for the purpose of detecting the oxygen or carbon dioxide concentration in circulating blood available in the vascular system in and just below the surface of the inner wall of the cheek. This location is favorable because it is inside the body and so is not subject to exterior temperature and atmospheric variations and because the blood flow near the surface of the interior skin covering of the cheek is easily utilized and is subject to augmentation and acceleration.

The mechanism involved includes a base plate assembly 11, as especially shown in FIG. 3, inclusive of a base plate 12. This plate is an approximately flat member of relatively inert material rounded on its edges and approximately elliptical in plan, as shown in FIG. 2. It is of a size easily to be received through the human mouth and when in position to lie against the upper and lower jaws alongside the outer side of the teeth and gums and to extend toward the jaw hinge and toward the frontal portion of the mouth. Because of its shape, the base plate 12 tends to fit into and to be retained in the desired location within close limits. Merging with the base plate 12 and included in the base plate assembly is a dome 14 of material comparable to that of the remainder of the base plate structure and hollow to leave room for a cartridge 16. This has an enlarged, generally circular base portion 18 fitted into a recess in the plate 12. It is capped by a similar circular cylindrical, integral top portion 19 of a smaller diameter affording an annular step 21.

Within the cartridge 16 there is positioned an outer, partly exposed electrode 22 in the shape of a ring and preferably of a noble metal such as gold. The ring is concentrically arranged within the top portion 19 and extends to and is exposed at the upper or outer surface thereof. Concentrically disposed within the electrode 22 is a co-acting electrode 23, preferably of a different noble metal, and similarly embedded in and surface exposed in the cartridge 16.

There are electrical conductors 24 and 25 respectively connected to the electrodes 22 and 23 and extending therefrom and through a cable 27 embedded in the base plate, as shown in FIG. 3. The cable 27 has a yieldable but fairly firm extension 28 of a sufficient length to extend from a position within the mouth of the user between his lips and from his mouth and to an external location and to an indicator. By manipulating the external part of the extension 28, some positional changes can be induced in the base plate assembly 11 and its associated structures.

Also mounted in the cartridge 16 is an electrical heating coil 31 included in a circuit containing conductors 32 and 33. These are likewise included in the cable 27 and extend outwardly to a suitable external source of electricity. When energized, the coil 31 increases the temperature of its surroundings and particularly of the adjacent area of the cheek 9. To regulate the amount of heat emanating from the coil, there is provided a detecting thermistor 37 connected in a circuit including conductors 38 and 39 likewise in the cable 27 and extending exteriorly to a suitable regulating and indicating device, not shown.

Unlike the exterior skin, which cannot properly withstand much increase in the normal temperature (around 42–44 degrees Centigrade), the inside of the mouth can, without injury and without pain, be increased in temperature to around 46–50 degrees Centigrade. This increased temperature produces vascular dilation and a substantial increase in blood flow. It also tends to establish a standard measuring condition so that successive trials are more nearly consistent than otherwise. The time necessary for a representative reading is also reduced markedly over an external skin measurement.

Covering much of the described structure when it is used within the body 16 is a cap-like shroud 41 of a gas permeable, thin, sanitary material that can easily be positioned, as shown, between the cartridge 16 and the surrounding portion of the dome 14. Preferably, the shroud 41 has an enlarged lower rim 42 interposed and, in effect, seated between the dome and the body 16 so that all of the parts are held in the desired, close relationship. The shroud is readily permeable to a gas such as oxygen from the blood and has very little insulating effect so far as the local heating is concerned.

This device in use is appropriately connected to the indicated source of power and to the desired indicators and controllers and is manipulated partly by use of the cable 27 into the patient's mouth so as to lodge, as shown in FIG. 1, with the electrodes adjacent the cheek and spaced therefrom only by the intervening shroud 41. The plate 11 assists in holding the detecting mechanism closely within the desired stationary location within the user's mouth, or at least in a small zone uniformly heated. Thus, the detection of the blood gas, such as oxygen, in that limited area is virtually invariable. There is no particular variation in blood gas detection, for there is only limited shifting of the responsive structure with respect to the contacting cheek surface. There is no pinching of the flesh and no restriction of vascular expansion. Desired manipulation of the device within the mouth is readily accomplished or assisted by operating the extension 28.

It is sometimes the practice to place the unit just before use in an external sanitary envelope 43. This is of relatively thin, easily deformable material effective to pass blood gas, such as oxygen, and not appreciably affecting the heat transfer characteristics. The envelope 43 can be changed between uses of the device, particularly if different individuals are concerned. When the device is in place, the blood gas or oxygen reading may continue for only a few moments or may be for many hours. The effect is to warm the adjacent interior skin of the cheek to an elevated temperature and to maintain the chosen temperature over a suitable, extended area and for any length of time in order to augment the local blood flow and to maintain a substantially standard environment for blood gas readings even though the device may shift position slightly.

It has been found that the interior surface of the cheek remains comfortable and is non-traumatically and quickly susceptible to a relatively high applied temperature. The device thus achieves a status suitable for accurate reading in a very short time, a matter of perhaps a minute or less. In many instances the device can simply be inserted, a reading taken in a relatively few minutes, and the device then removed. The device is sufficiently comfortable so that it can be left in place for hours at a time if continuous monitoring is desired. Although the patient may be well aware of a foreign object present in his mouth, there is no particular discomfort and no effect upon the internal mouth tissues when the device is removed.

Figure 5:
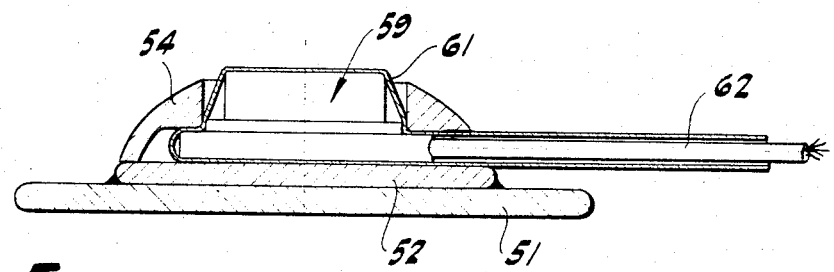
FIG. 5 is a cross-section, the plane of which is indicated by the lines 5—5 of FIG. 4.
Figure 6:
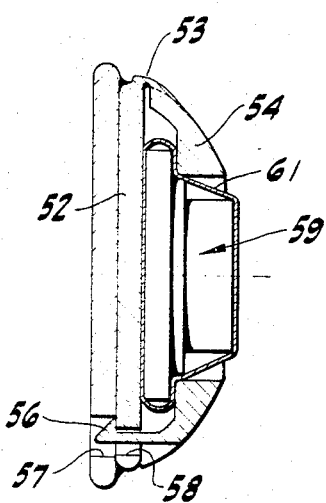
FIG. 6 is a cross-section, the plane of which is indicated by the line 6—6 of FIG. 4.

A comparable device is shown in FIGS. 4-6, in which the central portion of the mechanism is similar in having a base plate 51 of a generally elliptical or oval configuration in plan and a relatively thin depth dimension. To the base plate 51 is attached, preferably by a permanent adhesive, a superposed plate 52 of generally circular configuration. That plate 52 at one point has a flexible hinge 53 also attached to a hollow dome shell 54. These parts are normally held in closed position by a spring catch 56 operating through an opening 57 in the base plate 51 and engageable with an edge 58 of the plate 52. With this arrangement, when the catch 56 is released, the dome shell 54 can be swung out of the way or to one side of the plate 52 by movement about the hinge 53.

When the dome is so displaced or separated, a capsule 59 comparable to the previously described body 16 and containing the detecting and heating structures as disclosed in FIG. 3 can be positioned or removed. In this instance, the shroud 41 is replaced by a shroud 61 having the same general configuration as before but more extensive and continuing along a cable 62 comparable to the extension 28. At a convenient external point the electricity for the heater is furnished and the responsive devices for the heater and the indicating device for the blood gas, such as oxygen, are located. The conductors within the cable 62 are substantial duplicates of the conductors within the cable or extension 28.

In this form of the device as well as in the first form of the device, the dome structure and supporting plate are positioned between the outer sides of the user's jaw and the interior of his cheek with the dome against the inside skin of the cheek. The blood gas reading is displayed, being accelerated and facilitated by the heating element. This form of device can also be positioned and manipulated by the use of the extension 62. For successive uses the device may or may not receive different envelopes like the envelope 43. The shroud 61 is extra-firmly clamped in position when the dome is latched onto the base plate.

In both forms of the device there is provided a means readily received and retained in the human mouth between the exterior side of the jaws and the adjacent cheek interior for heating a local area of the cheek and for detecting blood gas, such as oxygen, in such location. While reference has been made to human use, for clarity of description herein, the device can also be adapted for similar veterinary and comparable usages.

We claim:

1. A blood gas detector comprising a positioning assembly including a flat base plate of approximately elliptical outline and of a thickness adapted to fit within the closed human mouth alongside and against both the upper and lower gums and the inside of the adjacent cheek and of a width to fit against the upper and lower merging portions of the inside of the cheek and the gums, a dome included in said positioning assembly and disposed on and projecting away from said base plate to displace the inside surface of said cheek to lie over said dome, a first sensing electrode disposed at the center of said dome and adapted to lie close to the inside of said cheek, a second sensing electrode disposed around the center of said dome spaced from and in electrical relationship with said first electrode and adapted to lie close to the inside of said cheek, and sensing electrical conductors respectively joined to said sensing electrodes and supported by and extending from said base plate.

2. A device as in claim 1 including an oxygen-permeable sheet on said assembly overlying said electrodes and adapted to lie against the inside of said cheek.

3. A device as in claim 1 in which said dome has an apex spaced from said base plate far enough to extend into cheek-displacing contact with the inside of said cheek and said electrodes being supported concentrically respectively at and near said apex so as to be positioned against the inside of said displaced cheek.

4. A blood gas detector as in claim 1 including an internal cable extension leading from said base plate for positioning within said mouth and having an external cable extension available on the exterior of said mouth, said extensions enclosing said electrical conductors and including means having stiffness effective for maneuvering said base plate within said mouth by motion of said extension outside said mouth.

5. A device as in claim 1 in which said dome is dimensioned to extend into contact with a relatively large area of the inside of said cheek and carries said electrodes adjacent the apex of said dome for contact with a relatively small area of the inside of said cheek, a heating coil disposed within said dome away from said apex, and means connected to said heating coil and effective to establish the temperature of the electrode-contacted area of said cheek at about 46–50 degrees Centigrade.

6. A device as in claim 5 including an envelope encasing said base plate and said dome, said envelope including a sheet of material for interposition between the inside of said cheek and said dome and overlying said apex to contact the adjacent displaced inside surface of said cheek, said sheet being of a material permeable by oxygen gas and permitting substantially unobstructed heat transfer between said apex and the adjacent displaced inside surface of said cheek.

7. A blood gas detector for use in the human mouth comprising a base plate of approximately elliptical contour and flat shape adapted to fit alongside the outside surfaces of the sides of the upper and lower jaws, means on said base plate for creating a firm extension of said base plate from inside the mouth to a location outside the mouth, a dome on said base plate for disposal within the mouth extend against and displace outwardly a portion of the cheek, means on said dome for heating an adjacent inside area of said portion of said cheek, electrodes disposed on said dome for contact with a heated portion of said cheek and means for electrically connecting said electrodes to a measuring circuit.

8. A method of detecting blood gas in circulating blood comprising inserting a body having a shape like a dome within the mouth and between the jaw and the inside of the cheek and thereby displacing the cheek outwardly away from the jaw and curved over the dome, disposing a pair of electrodes adjacent the apex of said dome and in substantial contact with the inside of said cheek, heating the inside area of said cheek surrounding said electrodes, and then determining the current value between said electrodes to indicate blood gas.

9. A method of detecting blood gas in circulating blood comprising placing a body against the inside of a cheek in a position to cause a portion of the cheek to curve over and against the body, positioning two electrodes in contact with the portion of the cheek, heating said portion of the cheek substantially above normal temperature, and determining the current value between said two electrodes in in substantial contact with the heated portion of the cheek to indicate blood gas.

* * * * *